(12) United States Patent
Ho

(10) Patent No.: US 6,902,670 B2
(45) Date of Patent: Jun. 7, 2005

(54) HEMODIALYSIS MACHINE

(76) Inventor: Kuo-Hsin Ho, 3F, No. 5, Lane 83, Sec. 1, Kuang Fu Rd., Sanchung City, Taipei Hsien (TW)

( * ) Notice: Subject to any disclaimer, the term of this patent is extended or adjusted under 35 U.S.C. 154(b) by 266 days.

(21) Appl. No.: 10/390,891

(22) Filed: Mar. 19, 2003

(65) Prior Publication Data

US 2004/0182773 A1 Sep. 23, 2004

(51) Int. Cl.$^7$ ............................ B01D 61/30; C02F 1/78
(52) U.S. Cl. .................... 210/252; 210/120; 210/257.1; 210/258; 210/321.71; 422/186.07; 204/176; 204/194
(58) Field of Search ................................. 210/120, 252, 210/257.1, 258, 321.71, 760; 204/164, 176, 194, 660; 422/186.04, 186.07

(56) References Cited

U.S. PATENT DOCUMENTS

| | | | |
|---|---|---|---|
| 5,585,003 A | * | 12/1996 | Van Newenhizen ......... 210/646 |
| 5,616,248 A | * | 4/1997 | Schal ......................... 210/647 |
| 6,146,536 A | * | 11/2000 | Twardowski ................ 210/646 |
| 6,551,474 B1 | * | 4/2003 | Andrews et al. ............ 204/266 |
| 6,585,898 B1 | * | 7/2003 | Ekberg et al. .............. 210/760 |
| 2002/0179518 A1 | * | 12/2002 | Ho ........................ 210/321.71 |
| 2003/0099584 A1 | * | 5/2003 | Diang et al. ........... 422/186.07 |

FOREIGN PATENT DOCUMENTS

GB      2 243 668 A    *   11/1991

* cited by examiner

*Primary Examiner*—John Kim
(74) *Attorney, Agent, or Firm*—Birch, Stewart, Kolasch, & Birch, LLP.

(57) ABSTRACT

A hemodialysis machine includes a purified water tube connected with at least one or tow water pumps in parallel. Each of the water pumps is connected with a reagent jug for taking reagent or disinfectant into water tubes so as to run dialysis process or sterilize tubes. The present invention features on that an ozone water device is coupled with a water inlet end of the purified water tube so that the ozone water is used to clean the tubes of the hemodialysis machine for avoiding the problem of disinfectant residuals.

4 Claims, 4 Drawing Sheets

HEMODIALYSIS MACHINE

BACKGROUND OF THE INVENTION

Field of the Invention

The present invention relates to hemodialysis machine, especially to a hemodialysis machine that produces ozone water for on-tube sterilization or for cleaning as well as resolving chemical residuals inside tubes after routine disinfection. The ozone water can not only fast sterilize tubes of the hemodialysis machine, but also clean the chemical residuals that may jeopardize the safety of hemodialysis patients.

Traditional hemodialysis device, as shown in FIG. 3, is constituted by a purified water tube (R.O. reverse osmosis water) 10 connected to at least one or two water pumps 21, 22 in parallel. Each of the water pumps 21, 22 is joined with a reagent jug 31, 32 respectively. The dialysate concentrate or disinfectant inside the reagent jugs 31, 32 is drawn into a solution tank 13 of the water tube 10 and is mixed with pure water thereof. A pump 14 takes the diluted dialysate from the solution tank 13, through the outlet end 11 of the water tube 10 to externals of a hemodialysis membrane 41 of an artificial kidney 41. A blood pump 51 takes the blood from the patient to the insides of the hemodialysis membrane 41 of the artificial kidney 41 and returns the blood to the patient via a blood circulation 50.

The concentration difference of the water and the pressure difference between the dialysate and the blood cause ion exchange thus push excess fluid out from the blood through the membranes into the dialysate. This is dialysis process.

However, after finishing a cycle of dialysis process, the water tube of the hemodialysis machine needs to be disinfected for preventing from infectious diseases. Conventional way of sterilization is by drawing disinfectants such as acetic acid or formalin into the water tube and then discharged the waste solution. Then a lot amount of water is used to wash the tubes. It takes a long period of time for sterilization by acetic acid or formalin. Moreover, even the tubes are washed again by water, there is still some residual acetic acid or formalin that may be harmful to the health of the next user. This is still a problem in medicine.

On Sep. 14, 1999, a prior art—"washing and disinfecting apparatus for artificial dialyzer using the acid water electrolytically made"—is disclosed. Refer to FIG. 4, the prior art includes a positive electrode and a negative electrode disposed inside a R.O. (reverse osmosis) water tank so as to electrolyze water for producing ozone gas that is turned back to the R.O. water tube. The shortcoming of this prior art is that the hydrogen from the negative electrode and the ozone from the positive electrode are easily to react and then turn back to water. Furthermore, the ozone gas is difficult to dissolve in pure water so that the concentration of the ozone concentration inside the solution of the hemodialysis device is less than 1 ppm. This leads to worse disinfectant effect. There is a need for improvement.

SUMMARY OF THE INVENTION

It is therefore a primary object of the present invention to provide a hemodialysis machine with convenient ozone sterilization function. The ozone has higher sterilization effects, no harm to human health, and easy to be reduced so that there is no problem of residuals. Thus the hemodialysis machine is safe for continuous users.

BRIEF DESCRIPTION OF THE DRAWINGS

The accomplishment of the above-mentioned object of the present invention will become apparent from the following description and its accompanying drawings which disclose illustrative an embodiment of the present invention, and are as follows.

DETAILED DESCRIPTION OF THE PREFERRED EMBODIMENT

Figure 1:
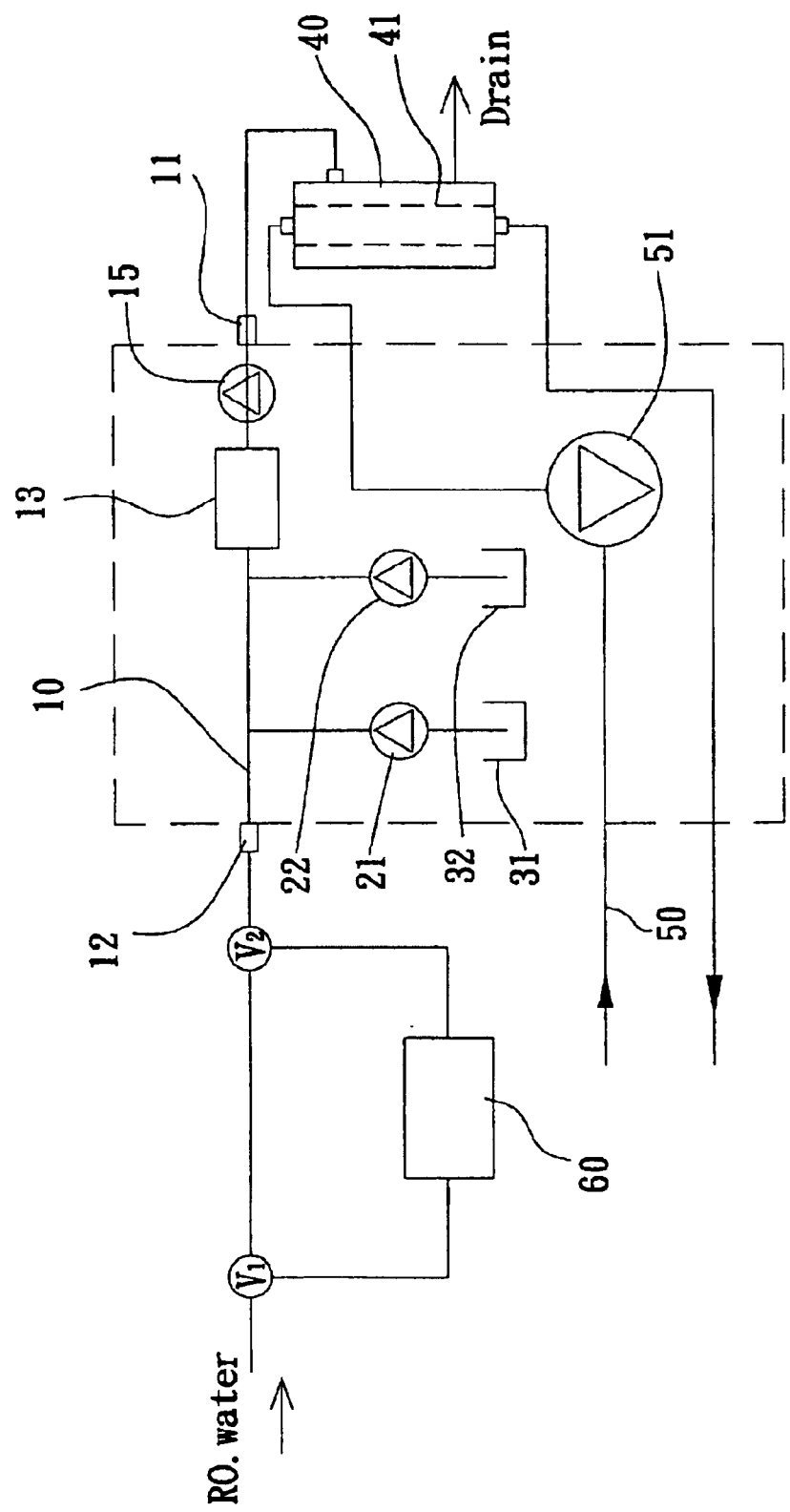
FIG. 1 is a high-pressure water supply system of the present invention.

A hemodialysis device includes at least one or two pumps 21, 22 connected with a purified water tube 10 in parallel. Each of the pumps 21, 22 is coupled with a reagent container 31, 32 respectively so as to draw reagents such as dialysis reagents into a storage tank 13 for dilution with R.O. water. A pump 15, through a water outlet end 11 of the purified water tube 10, is connected to an artificial kidney 40, outside a hemodialysis membrane 41. Inside the hemodialysis membrane 41 is blood from a blood circulation 50. Thus the infiltrative exchange happens between the hemodialysis solution and the blood. When the reagents is replaced by disinfectants, the purified water tube 10 is sterilized and then the waste is discharged.

Figure 2:
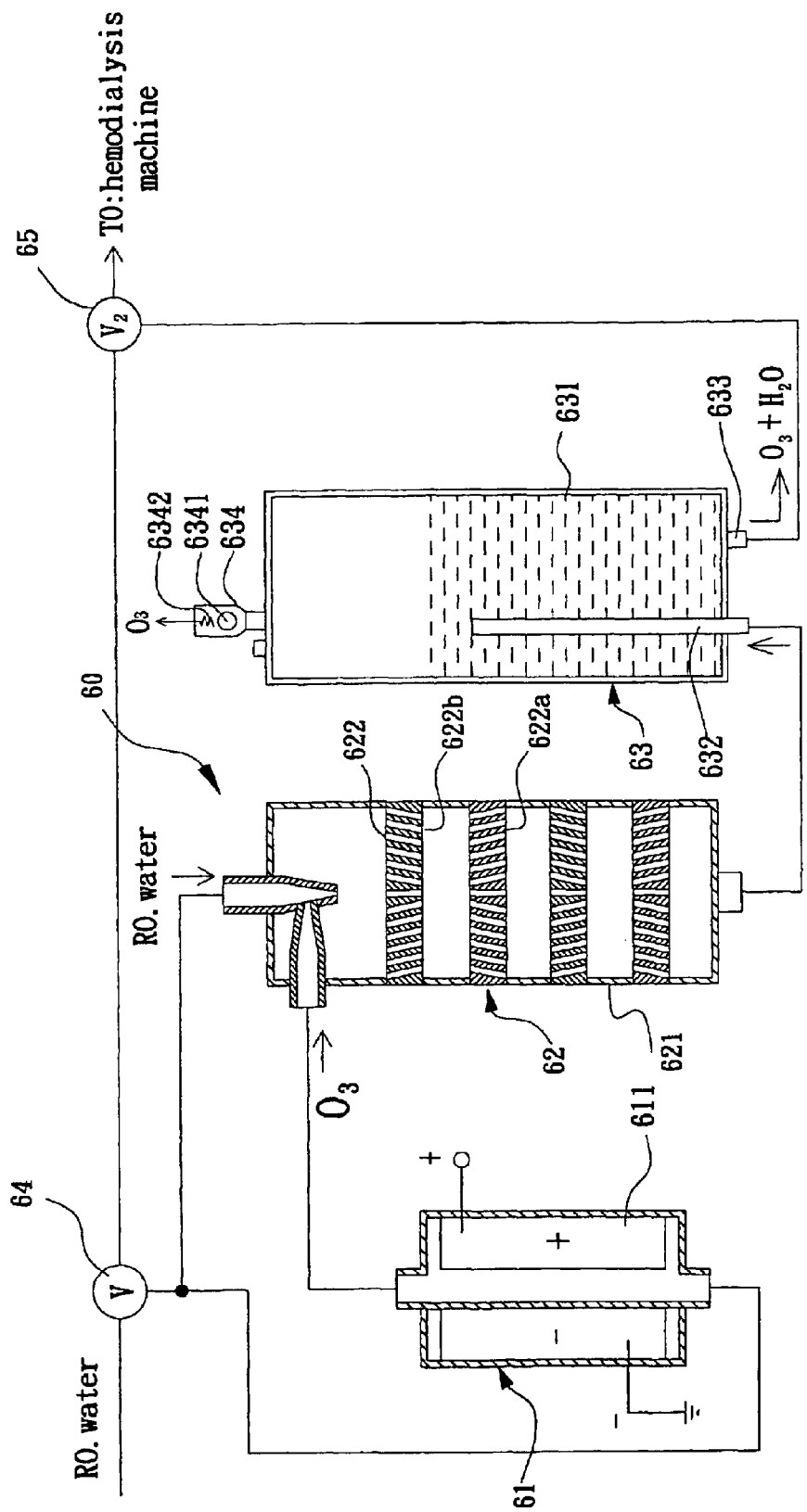
FIG. 2 is a schematic drawing of an ozone water device of the present invention.
Figure 3:
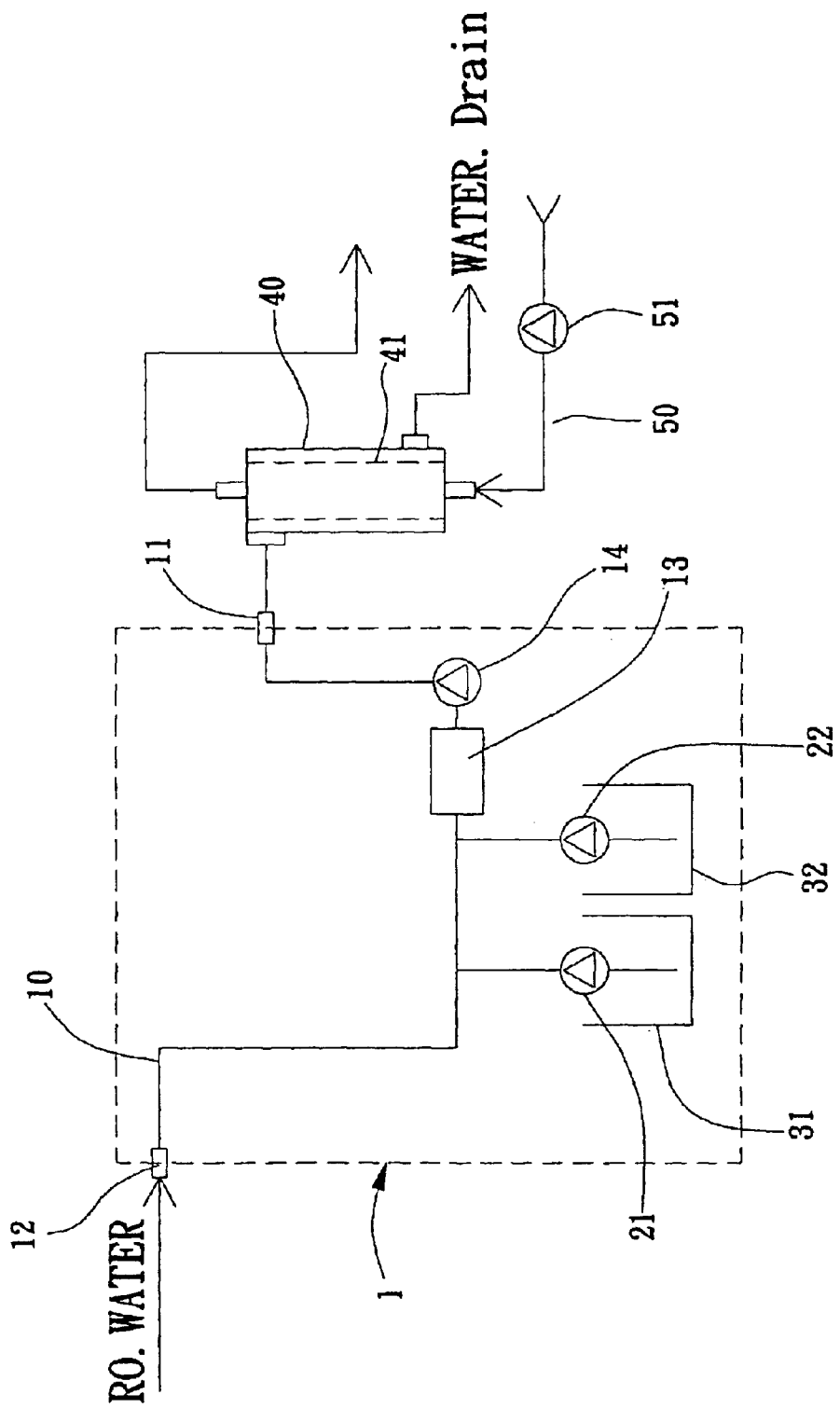
FIG. 3 is a high-pressure water supply system of a prior art.
Figure 4:
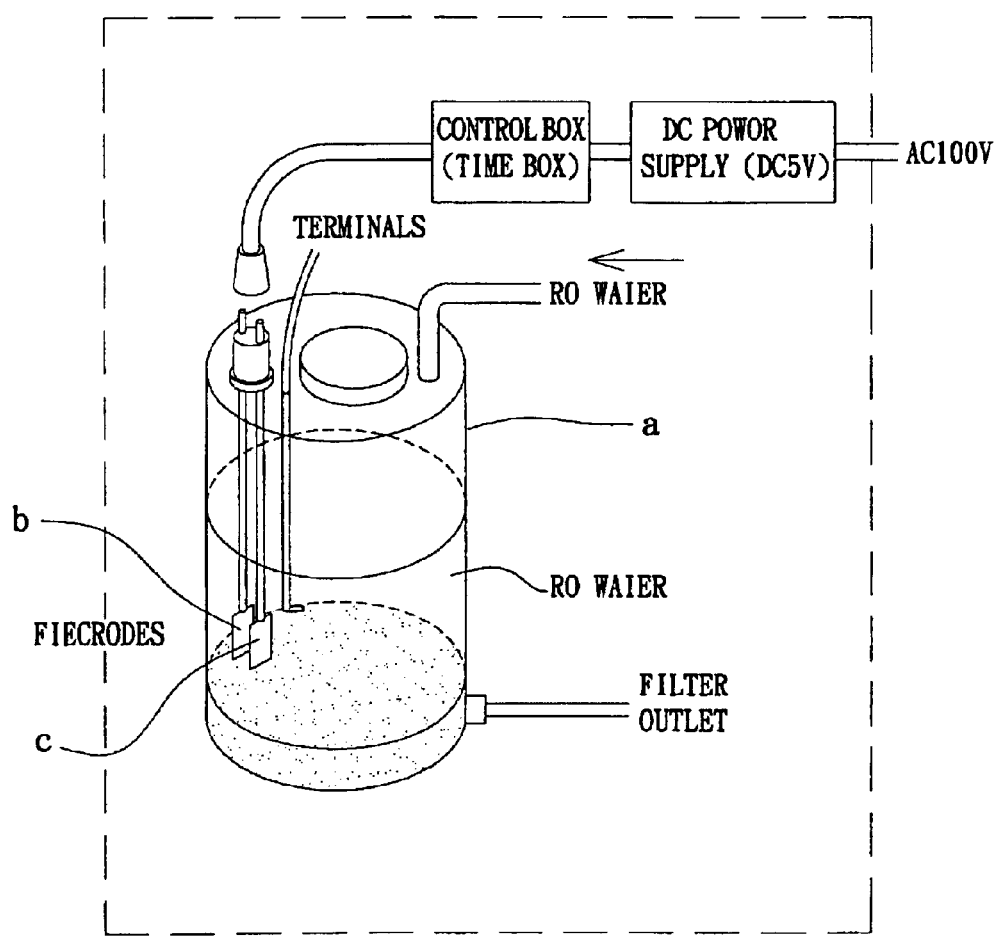
FIG. 4 is a perspective view of an embodiment of a prior art.

The device features on that an ozone water device 60, as shown in FIG. 2, is connected to a water inlet end 12 of the purified water tube 10. The ozone water device 60 includes at least an ozone generator 61, a mixer 62 and a storage tank 63 connected in series. Each valve 64, 65 is disposed on the inlet and outlet of the ozone water device 60 respectively and is coupled with the purified water tube 10 in parallel. Inside the ozone generator 61, only positive electrode contacts water and so that the R.O. water is electrolyzed and the ozone gas is produced. Then the ozone gas is dissolved in R.O. water by the mixer 62. Until the ozone concentration in R.O. water achieves certain degree, the ozone water (O3+H2O) is kept inside the storage tank 63. When being used, the valve 65 is opened and the ozone water flows from the storage tank 63 into the purified water tube 10 so as to dilute the dialysis reagent or cleaning (disinfecting) the purified water tube 10.

The mixer 62 is composed by a barrel 621 and a plurality layer of baffle 622. A plurality of small pores 622a, 622b inclined outwards or inwards, is disposed on the baffle 622. The baffles 622 with pores 622a, 622b inclined in different direction are arranged alternately. Thus when the ozone gas together with the R.O. water are infused from the inlet of the mixer 62, the duration for mixing gas and water is prolonged and the volume of ozone gas bubble is divided into smaller one. Therefore, the ozone concentration inside the water is increased (over 3–6 ppm).

On the bottom of a container 631 of the storage tank 63, a water inlet tube 632 and a water outlet tube 633 are arranged thereof. A gas outlet 634 with a steel ball 6341 and a spring mechanism 6342 is arranged on the top of the container 631. The water inlet tube 632 extends from the bottom to the inner side of the container 631 to make the ozone water from the mixer 62 being stored inside the container 631 temporarily and the ozone bubble indissoluble in the water be separated from the ozone solution. Thus there is no bubble inside the purified water tube 10. When the pressure of the gas inside the container 631 achieves certain degree, by the manual or automatic action of the steel ball 6341 and the spring mechanism 6342, the gas will be displaced.

The ozone gas is a kind of active gas that is easy to react with other material, thus with higher sterilization effect than any other chemicals and no problem of residual. While directly contacting human blood, the ozone can even kill bacterium in blood. Therefore, the ozone water produced by the ozone water device 60 can be infused and mixed with dialysate reagents for the use of hemodialysis. Moreover, when the hemodialysis machine needs to be sterilized, high concentration ozone water is used for antisepsis instead of chemical disinfectants. Or after chemical sterilization, the ozone water is used to wash the tubes for cleaning residual chemicals.

It should be noted that the above description and accompanying drawings are only used to illustrate some embodiments of the present invention, not intended to limit the scope thereof. Any modification of the embodiments should fall within the scope of the present invention.

What is claimed is:

1. A hemodialysis machine comprising at least a pump connected with a purified water tube in parallel; each of said pump coupled with a reagent container so as to draw reagents inside said reagent container for dilution and diluted reagents passing through a water outlet end of said purified water tube to an artificial kidney for infiltrative exchange with blood or sterilization of said purified water tube; wherein the improvement of the present invention is characterized in that an ozone water device having at least an ozone generator, a mixer and a storage tank connected in series is connected to a water inlet end of said purified water tube; a valve is disposed on the inlet and outlet end of said ozone water device respectively and is coupled with said purified water tube in parallel; inside said ozone generator, only a positive electrode contacts water and so that purified water is electrolyzed thus ozone gas is produced and dissolved in purified water by said mixer, then flows into said storage tank.

2. The hemodialysis machine as claimed in claim 1, wherein said mixer includes a plurality layer of baffle with a plurality of small pore inclined outwards or inwards; said layer of baffles with said pores inclined in different direction are arranged alternately.

3. The hemodialysis machine as claimed in claim 1, wherein a water inlet tube and a water outlet tube are arranged on bottom of a container of said storage tank; a gas outlet is disposed on top of said container; said water inlet tube extends from the bottom to the inner side of said container.

4. The hemodialysis machine as claimed in claim 1, wherein a steel ball and a spring mechanism is arranged on said gas outlet.

* * * * *